(12) United States Patent
Jung et al.

(10) Patent No.: US 7,941,205 B2
(45) Date of Patent: May 10, 2011

(54) SYSTEM AND METHOD FOR SEPARATING CARDIAC SIGNALS

(75) Inventors: Tzyy-Ping Jung, San Diego, CA (US); Jeng-Ren Duann, San Diego, CA (US)

(73) Assignee: Sigmed, Inc., San Diego, CA (US)

( * ) Notice: Subject to any disclaimer, the term of this patent is extended or adjusted under 35 U.S.C. 154(b) by 556 days.

(21) Appl. No.: 10/482,931

(22) PCT Filed: Jul. 3, 2002

(86) PCT No.: PCT/US02/21277
§ 371 (c)(1),
(2), (4) Date: Sep. 9, 2004

(87) PCT Pub. No.: WO03/003905
PCT Pub. Date: Jan. 16, 2003

(65) Prior Publication Data
US 2005/0010120 A1 Jan. 13, 2005

Related U.S. Application Data

(60) Provisional application No. 60/303,325, filed on Jul. 5, 2001.

(51) Int. Cl.
*A61B 5/0452* (2006.01)
(52) U.S. Cl. ......... 600/509; 600/515; 600/518; 600/523
(58) Field of Classification Search .................. 600/508, 600/515, 518, 523
See application file for complete search history.

(56) References Cited

U.S. PATENT DOCUMENTS

| 4,974,568 | A | * | 12/1990 | Cser | 123/184.57 |
|---|---|---|---|---|---|
| 5,042,499 | A | * | 8/1991 | Frank et al. | 600/511 |
| 5,201,321 | A | * | 4/1993 | Fulton | 600/515 |
| 5,423,863 | A | * | 6/1995 | Felblinger et al. | 607/5 |
| 5,706,402 | A | * | 1/1998 | Bell | 706/22 |
| 5,967,995 | A | * | 10/1999 | Shusterman et al. | 600/516 |
| 6,389,308 | B1 | * | 5/2002 | Shusterman | 600/509 |
| 6,424,960 | B1 | * | 7/2002 | Lee et al. | 706/20 |
| 7,092,748 | B2 | | 8/2006 | Valdes Sosa et al. | |
| 2004/0193064 | A1 | | 9/2004 | Shusterman | |
| 2004/0243015 | A1 | * | 12/2004 | Smith et al. | 600/511 |
| 2005/0007091 | A1 | * | 1/2005 | Makeig et al. | 324/76.13 |

OTHER PUBLICATIONS

Vigário. "Extraction of ocular artifacts from EEG using independent component analysis." Electroencephalography and clinical Neurophysiology; 103 (1997): 395-404.*

* cited by examiner

*Primary Examiner* — Scott M Getzow
*Assistant Examiner* — Joseph M Dietrich
(74) *Attorney, Agent, or Firm* — Anatoly S. Weiser; Daniel M. Chambers; Acuity Law Group

(57) ABSTRACT

EKG sensors ((150) are placed on a patient (140) to receive electrocardiogram (EKG) recording signals, which are typically combinations of original signals from different sources, such as pacemaker signals, QRS complex signals, and irregular oscillatory signals that suggest an arrhythmia condition. A computing module (120) uses independent component analysis to separate the recorded EKG signals. The separated signals are displayed to help physicians to analyze heart conditions and to identify probably locations of abnormal heart conditions. At least a portion of the separated signals can be further displayed in a chaos phase space portrait to help detect abnormality in heart conditions.

15 Claims, 7 Drawing Sheets

SYSTEM AND METHOD FOR SEPARATING CARDIAC SIGNALS

BACKGROUND OF THE INVENTION

CROSS REFERENCE TO RELATED APPLICATION

The present application is the U.S. national stage application of International Application PCT/US02/21277, filed Jul. 3, 2002, which was published on Jan. 16, 2003 as International Publication Number WO 03/003905.

1. Field of the Invention

The present invention relates to medical devices for recording cardiac signals and separating the recorded cardiac signals.

2. Description of the Related Art

Electrocardiogram (EKG) recording is a valuable tool for physicians to study patient heart conditions. In a typical 12-lead arrangement, up to 12 sensors are placed on a subject's chest or abdomen and limbs to record the electric signals from the beating heart. Each sensor, along with a reference electrode, form a separate channel that produces an individual signal. The signals from the different sensors are recorded on an EKG machine as different channels. The sensors are usually unipolar or bipolar electrodes or other devices suitable for measuring the electrical potential on the surface of a human body. Since different parts of the heart, such as the atria and ventricles, produce different spatial and temporal patterns of electrical activity on the body surface, the signals recorded on the EKG machine are useful for analyzing how well individual parts of the heart are functioning.

A typical heartbeat signal has several well-characterized components. The first component is a small hump in the beginning of a heartbeat called the "P-Wave". This signal is produced by the right and left atria. There is a flat area after the P-Wave which is part of what is called the PR Interval. During the PR interval the electrical signal is traveling through the atrioventricular node (AV) node. The next large spike in the heartbeat signal is called the "QRS Complex." The QRS Complex is tall, spikey signal produced by the ventricles. Following the QRS complex is another smaller bump in the signal called the "T-Wave," which represents the electrical resetting of the ventricles in preparation for the next signal. When the heart beats continuously, the P-QRS-T waves repeat over and over.

Many publications have described studying cardiac signals and detecting abnormal heart conditions. Sample publications include U.S. Patent Publication No. 20020052557; Podrid & Kowey, *Cardiac Arrhythmia: Mechanisms, Diagnosis, and Management* Lippincott Williams & Wilkins Publishers (2nd edition, Aug. 15, 2001); Marriott & Conover, *Advanced Concepts in Arrhythmias*, Mosby Inc. (3nd edition, Jan. 15, 1998); and Josephson, M. E., *Clinical Cardiac Electrophysiology: Techniques and Interpretations*, Lippincott Williams & Wilkins Publishers; ISBN (3rd edition, Dec. 15, 2001).

Unfortunately, although EKG signals have been studied for decades, they are difficult to assess because EKG signals recorded at the surface are mixtures of signals from multiple sources. Typically, it is relatively straightforward to measure the shape of the QRS complex since this signal is so strong. However, irregular shaped P-wave or T-wave signals, along with weak irregular oscillatory signals that suggest a heart arrhythmia are often masked by large pacemaker signals, or the strong QRS complex signals. Thus, it can be very difficult to isolate small irregular oscillatory signals and to identify arrhythmia conditions.

In addition, atrial and ventricular signals are sometimes undesirably superimposed over one another. In many cases, diagnosis of disease states requires these signals to be separated from one another. For example, it might be desirable to separate P wave signals from QRS complex signals, so that signals originating in an atrium are isolated from signals representing concurrent activities in the ventricle.

In some practices the EKG signals are electronically "filtered" by excluding signals of certain frequencies. The signals are also "averaged" to remove largely random or asynchoronous data, which is assumed to the meaningless "noise." The filtering and averaging methods irreversibly eliminate portions of the recorded signals. In addition, it is not proven whether the more random data is truly "noise" and truly meaningless. It might be that the signals that are removed are indicative of a disease state in a patient. Another method as disclosed in U.S. Pat. No. 6,308,094 entitled "System for prediction of cardiac arrhythmias" uses Karhunen Loeve Transformation to decompose or compress cardiac signals into elements that are deemed "significant." As a result the information that are deemed "insignificant" are lost.

Compared to other signal separation applications, separating EKG recording signals presents additional challenges. For example, the sources are not always stationary since the heart chambers contract and expand during beating. Additionally, the activity of a single chamber may be mistaken for multiple sources because of the presence of moving waves of electrical activity across the heart. If electrodes are not securely attached to the patient, or if the patient moves (for example older patients may suffer from uncontrolled jittering), the movement of the electrodes also undesirably generates signals. In addition, multiple signals can be sensed by the EKG which are unrelated to the cardiac signature, such as myopotentials, i.e., electrical signals from muscles other than the heart.

There has been disclosure of cardiac rhythm management systems that store of list of triggers. U.S. Pat. No. 6,400,982 entitled "Cardiac rhythm management system with arrhythmia prediction and prevention" discloses such a system. If a trigger matches detected cardiac signals from a patient, the system calculates the probability of arrhythmia and activates a prevention therapy to the patient. However the cardiac signals are in fact mixtures of signals from multiple sources, and the signals that are important for arrhythmia detection can be masked by other signals. It is therefore desirable to separate the cardiac signals used in the cardiac rhythm management systems.

Independent component analysis (ICA) is a technique for separating mixed source signals (components) which are presumably independent from each other. In its simplified form, independent component analysis operates a "un-mixing" matrix of weights on the mixed signals, for example multiplying the matrix with the mixed signals, to produce separated signals. The weights are assigned initial values, and then adjusted to minimize information redundancy in the separated signals. Because this technique does not require information on the source of each signal, it is known as a "blind source separation" method. Blind separation problems refer to the idea of separating mixed signals that come from multiple independent sources. Although there are many ICA techniques currently known, most have evolved from the original work described in U.S. Pat. No. 5,706,402 issued on Jan. 6, 1998. Additional references of ICA and blind source separation can be found in, for example, A. J. Bell and T J Sejnowski, *Neural Computation* 7:1129-1159 (1995)); Te-Won Lee, *Independent Component Analysis: Theory and Applications*, Kluwer Academic Publishers, Boston, September 1998, Hyvarinen et al., *Independent Component Analysis,* 1st edition (Wiley-Interscience, May 18, 2001); Mark Girolami, *Self-Organizing Neural Networks: Independent Component Analysis and Blind Source Separation* (Perspectives in Neural Computing) (Springer Verlag, September 1999); and Mark Girolami (Editor), *Advances in Independent Component Analysis* (Perspectives in Neural Computing) (Springer Verlag August 2000). Single value decomposition algorithms have been disclosed in *Adaptive Filter Theory* by Simon Haykin (Third Edition, Prentice-Hall (NJ), (1996).

There has been suggestion to use chaos theory to analyze cardiac signals to detect abnormal heart conditions. Sample disclosures include U.S. Pat. Nos. 5,439,004, 5,342,401, 5,447,520 and 5,456,690; PCT application Nos. WO02/34123 and WO0224276; Smith et al. *Electrical Alternans and Cardiac Electrical Instability*. Circulation, Vol. 77, No. 1, pp. 110-121 (January 1988). Other approaches are disclosed in U.S. Pat. No. 5,447,520 issued to Spano, et al. and U.S. Pat. No. 5,201,321 issued to Fulton. Chaos theory is defined as the study of complex nonlinear dynamic systems. Complex implies just that, nonlinear implies recursion and higher mathematical algorithms, and dynamic implies non-constant and non-periodic. Thus chaos theory is, very generally, the study of changing complex systems based on mathematical concepts of recursion, whether in the form of a recursive process or a set of differential equations modeling a physical system.

When a bounded chaotic system has some kind of long-term pattern, but the pattern is not a simple periodic oscillation or orbit, then the system has a "Strange Attractor". If the system's behavior is plotted in a graph over an extended period patterns can be discovered that are not obvious in the short term. In addition, in these types of systems, no matter what the initial conditions are, usually the same pattern is found to emerge. The area for which this recurring pattern holds true is called the "basin of attraction" for the attractor. Chaos theory methods have been described in, for example, N. H. Packard, J. P. Crutchfield, J. Doyne Farmer, and R. S. Shaw, *Geometry of a Time Series*, Physical Review Letters, 47 (1980), p. 712; F. Takens, *Detecting Strange Attractors in Turbulence* in Lecture Notes in Mathematics 898, D. A. Rand and L. S. Young, eds., (Berlin: Springer-Verlag, 1981), p. 336; and J. P. Crutchfield, J. Doyne Farmer, N. H. Packard, and R. S. Shaw, *On Determining the Dimension of Chaotic Flows*, Physica 3D, (1981), pp. 605-17.

For all of these reasons, what is needed in the art is a system that can accurately separate medical signals from one another in order to diagnose disease states.

SUMMARY OF THE INVENTION

The present application discloses systems and methods for using independent component analysis to determine the existence and location of anomalies such as arrhythmias of a heart. The disclosed systems and methods can be applied to suggest the location of atrial fibrillation, and to locate arrhythmogenic regions of a chamber of the heart using heart cycle signals measured from a body surface of the patient. Non-invasive localization of the ectopic origin allows focal treatment to be quickly targeted to effectively inhibit these complex arrhythmias without having to rely on widespread and time consuming sequential searches or on massively invasive simultaneous intracardiac sensor technique. The effective localization of these complex arrhythmias can be significantly enhanced by using independent component analysis to separate superimposed heart cycle signals originating from differing chambers or regions of the heart tissue. In addition, the signals that are separated by ICA are preferably also analyzed by plotting them on a chaos phase space portrait.

One aspect of the invention relates to a medical system for separating cardiac signals. This aspect includes a receiving module to receive recorded cardiac signals from medical sensors, a computing module to separate the received signals using independent component analysis to produce separated signals, and a display module to display the separated signals.

Another aspect of the invention relates to a method of detecting arrhythmia in a patient. The method includes placing EKG sensors on a patient to produce recorded EKG signals, sending the recorded signals to a computing module to separate the recorded signals into separated signals using independent component analysis, and reviewing a display of the separated signals to determine the existence of arrhythmia in the patient. In a preferred embodiment, each component of separated signals corresponds to a channel of recorded signals and its sensor location, therefore when the one or more components of separated signals that suggest arrhythmia are detected, the corresponding one or more sensor locations also suggest the location of arrhythmia.

Yet another aspect of the invention relates to a cardiac rhythm management system. The system includes a cardiac signal recording module to record cardiac signals of a patient, a computing module to separate the recorded signals into separated signals using independent component analysis, and a detection module to detect or to predict an abnormal condition based on analyzing the separated signals. The system also includes a treatment module to treat the patient or a warning module to issue a warning when the abnormal condition is detected or predicted.

Other aspects and embodiments of the invention are described below in the detailed description section or defined by the claims.

DETAILED DESCRIPTION OF THE PREFERRED EMBODIMENT

Embodiments of the invention relate to a system and method for accurately separating medical signals in order to determine disease states in a patient. In one embodiment, the system analyzes EKG signals in order to determine whether a patient has a heart ailment or irregularity. As discussed in detail below, embodiments of the system utilize the techniques of independent component analysis to separate the medical signals from one another.

In addition to the signal separation technique, embodiments of the invention also relate to systems and methods that first separate signals using ICA, and then perform an analysis on a specific isolated signal, or set of isolated signals, using a "chaos" analysis. As described earlier, Chaos theory (also called nonlinear dynamics) studies patterns that are not completely random, but cannot be determined by simple formulas. Because cardiac signals are typically non-random, but cannot be easily described by a simple formula, Chaos theory analysis as described below provides an effective tool to analyze these signals and determine disease states.

Accordingly, once the signals are separated using ICA, they can be plotted to produce a chaos phase space portrait. By reviewing the patterns in the phase space portrait, for example reviewing the existence and location of one or more attractors, or comparing established health patterns and established abnormal patterns with the patterns of the patient, a user is able to assess the likelihood of abnormality in the signals, which indicate disease conditions in the patient.

Figure 1:
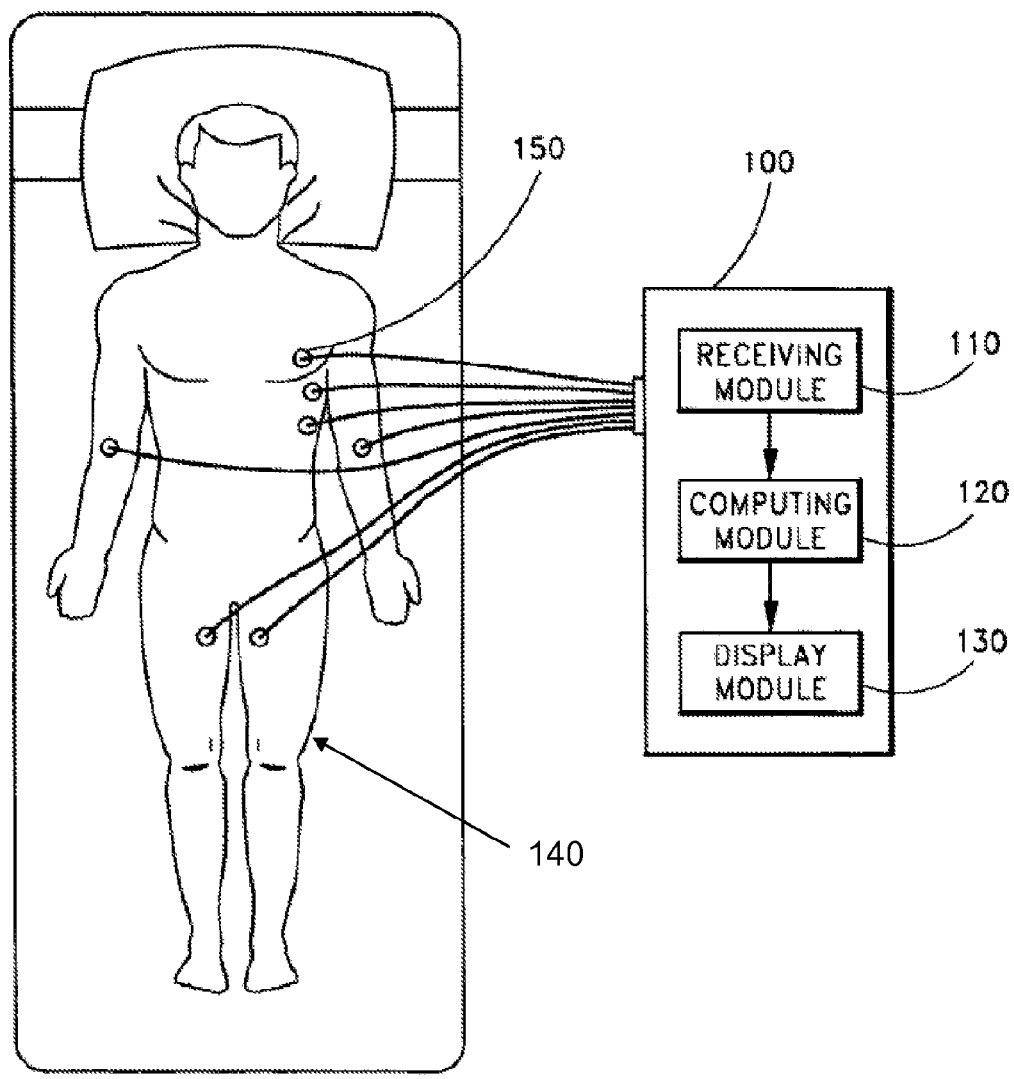
FIG. 1 is a diagram of a EKG system according to one embodiment of the invention.

FIG. 1 is a diagram of an EKG system that includes a computing module for signal separation according to one embodiment of the present invention. As shown in FIG. 1, electrode sensors 150 are placed on the chest and limb of a patient 140 to record electric signals. The electrodes send the recorded signals to a receiving module 110 of the EKG system 100. After optionally performing signal amplification, analog-to-digital conversion or both, the receiving module 110 sends the received signals to a computing module 120 of the EKG system 100. The computing module 120 uses an independent component analysis method to separate the recorded signals to produce separated signals. The independent component analysis method has been described in detail in the Appendix and below with respect to FIG. 2.

The computing module 120 can be implemented in hardware, software, or a combination of both. It can be located physically within the EKG system 100 or connected to the recorded signals received by the EKG system 100. A displaying module 130, which includes a printer or a monitor, displays the separated signals on paper or on screen. The displaying module 130 can be located within the EKG system 100 or connected to it. Optionally, the displaying module 130 also displays the recorded signals on paper or on screen. In one embodiment, the displaying module also displays some components of the separated signals in a chaos phase space portrait.

In one embodiment, the EKG system 100 also includes a database (not shown) that stores recognized EKG signal triggers and corresponding diagnosis. The triggers refer to conditions that indicate the likelihood of arrhythmia. For example, triggers can include sinus beats, premature sinus beats, beats following long sinus pauses, long-short beat sequences, R on T-wave beats, ectopic ventricular beats, premature ventricular beats, and so forth. Triggers can include threshold values that indicate arrhythmia, such as threshold values of ST elevations, heart rate, increase or decrease in heart rate, late-potentials, abnormal autonomic activity, and so forth. A left bundle-branch block diagnosis can be associated with triggers such as the absence of q wave in leads I and V6, a QRS duration of more than 120 msec, small notching of R wave, etc.

Triggers can be based on a patient's history, for example the percentage of abnormal beats detected during an observation period, the percentage of premature or ectopic beats detected during an observation period, heart rate variation during an observation period, and so forth. Triggers may also include, for example, the increase or decrease of ST elevation in beat rate, the increase in frequency of abnormal or premature beats, and so forth.

A matching module (not shown) attempts to match the separated signals with one or more of the stored triggers. If a match is found, the matching module displays the matched corresponding diagnosis, or sends a warning to a healthcare worker or to the patient. Methods such as computer-implemented logic rules, classification trees, expert system rules, statistical or probability analysis, pattern recognition, database queries, artificial intelligence programs and others can be used to match the separated signals with stored triggers.

Figure 2:
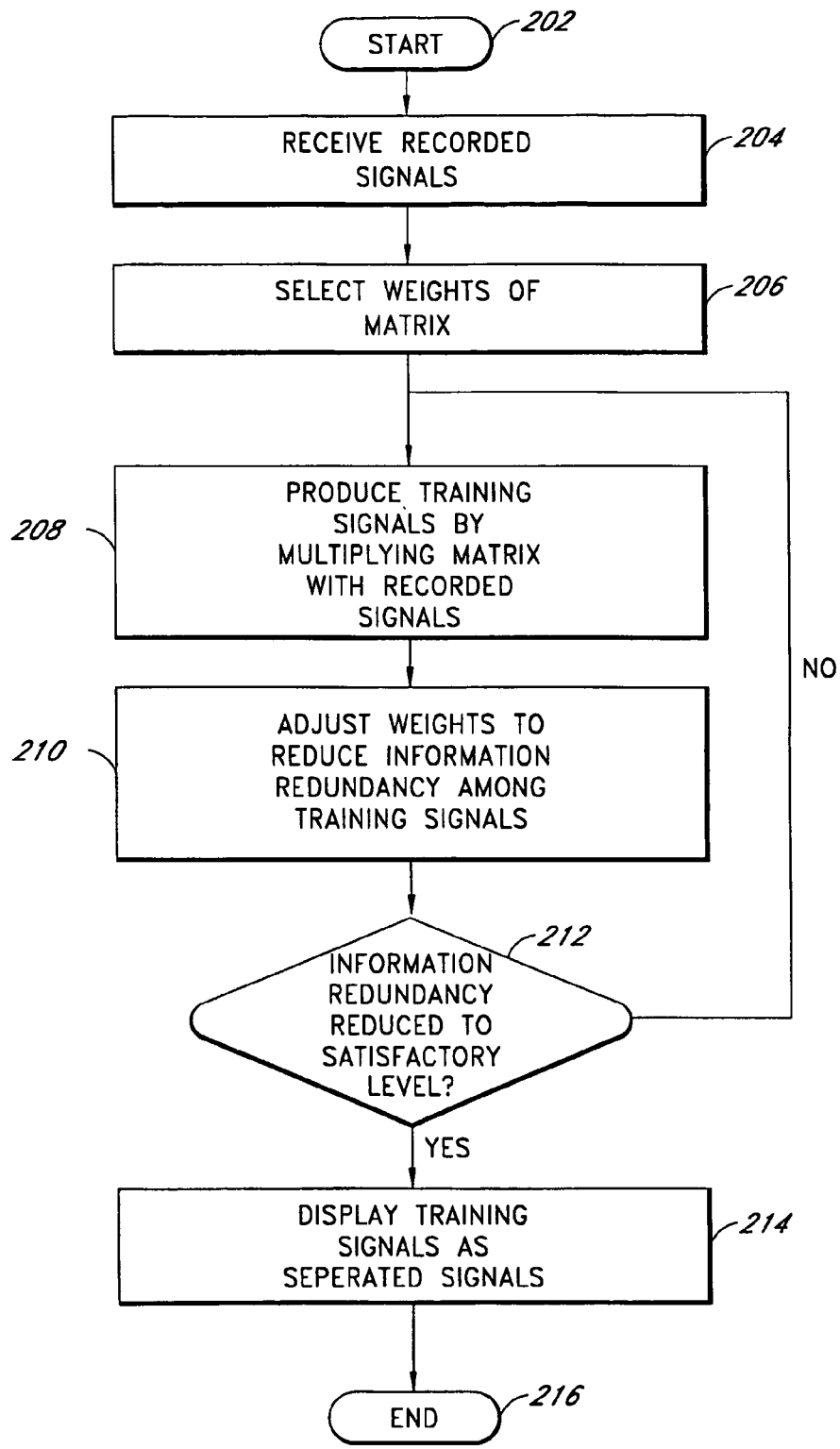
FIG. 2 is a flowchart illustrating one embodiment of a process for separating cardiac signals.

FIG. 2 is a flowchart illustrating one embodiment of a process for separating EKG signals. The process starts from a start block 202, and proceeds to a block 204, where the computing module 120 of the EKG system 100 receives the recorded signals $X_j$ from the electrode sensors, with J being the number of channels. Prior to processing, the signals can be amplified to strengths suitable for computer processing. Analog-to-digital conversion of signals can also be performed.

From the block 204, the process proceeds to a block 206, where the initial values for a "un-mixing" matrix of scaling weights $W_{ij}$ are selected. In one embodiment, the initial values for a matrix of initial weights $W_{i0}$ are also selected. The process then proceeds to a block 208, where a plurality of training signals $Y_i$ are produced by operating the matrix on the recorded signals. In a preferred embodiment, the training signals are produced by multiplying the matrix with the recorded signals such that $Y_i=W_{ij}*X_j$. In one embodiment, the initial weights $W_{i0}$ are included such that $Y_i=W_{ij}*X_j+W_{i0}$. The process proceeds from the block 208 to a block 210, wherein the scaling weights $W_{ij}$ and optionally the initial weights $W_{i0}$ are adjusted to reduce the information redundancy among the training signals. Methods of adjusting the weights have been described in the Appendix.

The process proceeds to a decision block 212, where the process determines whether the information redundancy has been reduced to a satisfactory level. The criteria for the determination has been described in the Appendix. If the process determines that information redundancy among the training signals has been reduced to a satisfactory level, then the process proceeds to a block 214, where the training signals are displayed as separated signals $Y_i$, with I being the number of components for the separated signals. In a preferred embodiment, I, the number of components of separated signals, is equal to J, the number of channels of recorded signals. Otherwise the process returns from the block 212 to the block 208 to again adjust the weights. From the block 214, the process proceeds to an end block 216.

For the un-mixing matrix W with the final weight values, its rows represent the time courses of relative strengths/activity levels (and relative polarities) of the respective separated components. Its weights give the surface topography of each component, and provide evidence for the components' physiological origins. For the inverse of matrix W, its columns represent the relative projection strengths (and relative polarities) of the respective separated components onto the channels of recorded signals. The back projection of the ith independent component onto the recorded signal channels is given by the outer product of the ith row of the separated signals matrix with the ith column of the inverse un-mixing matrix, and is in the original recorded signals. Thus cardiac dynamics or activities of interest accounted for by single or by multiple components can be obtained by projecting one or more ICA components back onto the recorded signals, $X=W^{-1}*Y$, where Y is the matrix of separated signals, $Y=W*X$.

The separated signals are determined by the ICA method to be statistically independent and are presumed to be from independent sources. Regardless of whether there is in fact some dependence between the separated EKG signals, test results show that the separated signals provide a beneficial perspective for physicians to detect and to locate the abnormal heart conditions of a patient.

In a preferred embodiment, time-delay between source signals is ignored. Since the sampling frequencies of cardiac signals are in the relatively low 200-500 Hz range, the effect of time-delay can be neglected.

Improved methods of ICA can be used to speed up the signal separation process. In one embodiment, a generalized Gaussian mixture model is used to classify the recorded signals into mutually exclusive classes. The classification methods have been disclosed in U.S. patent application Ser. No. 09/418,099 titled "Unsupervised adaptation and classification of multiple classes and sources in blind source separation" and PCT Application No. W00127874 titled "Unsupervised adaptation and classification of multi-source data using a generalized Gaussian mixture model." In another embodiment, the computing module 120 incorporates a priori knowledge of cardiac dynamics, for example supposing separated QRS components to be highly kurtotic and (ar)rythmic component(s) to be sub-Gaussian. ICA methods with incorporated a priori knowledge have been disclosed in T-W. Lee, M. Girolami and T. J. Sejnowski, Independent Component Analysis using an Extended Infomax Algorithm for Mixed Sub-Gaussian and Super-Gaussian Sources, Neural Computation, 1999, Vol.11(2): 417-441.

Figure 3A:
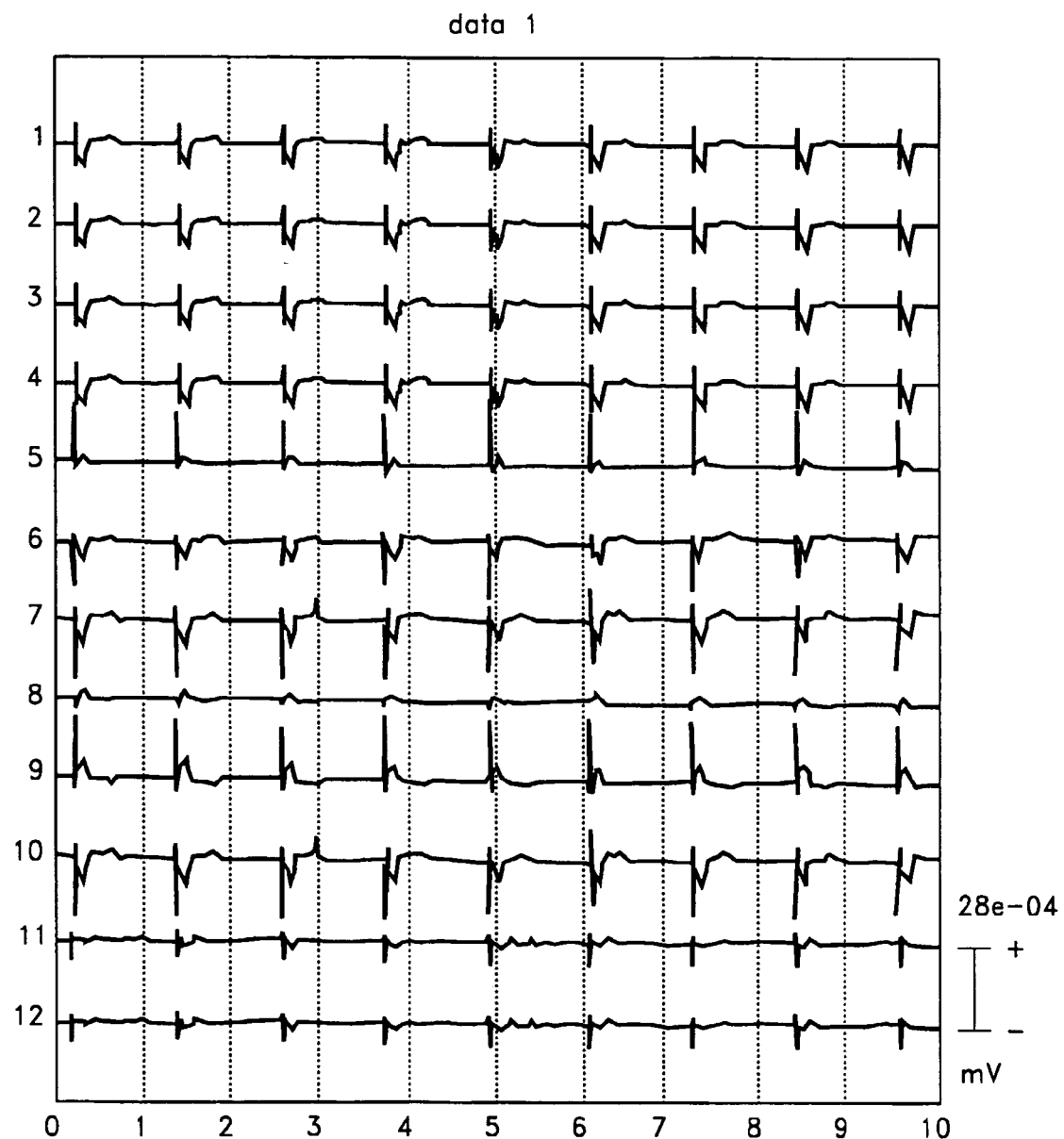
FIG. 3A is a sample chart of recorded EKG signals.

FIG. 3A illustrates a ten-second portion of 12 channels of signals that were gathered as part of an EKG recording. The horizontal axis in FIG. 3A represents time progression of ten seconds. The vertical axis represents channel numbers 1 to 12. The signals of FIG. 3A are, in this case, from a patient that provided a mixture of multiple signals, including QRS complex signals, pacemaker signals, multiple oscillatory activity signals, and noise. However, because these signals were all occurring simultaneously, they cannot be easily separated from one another using conventional EKG equipment.

Figure 3B:
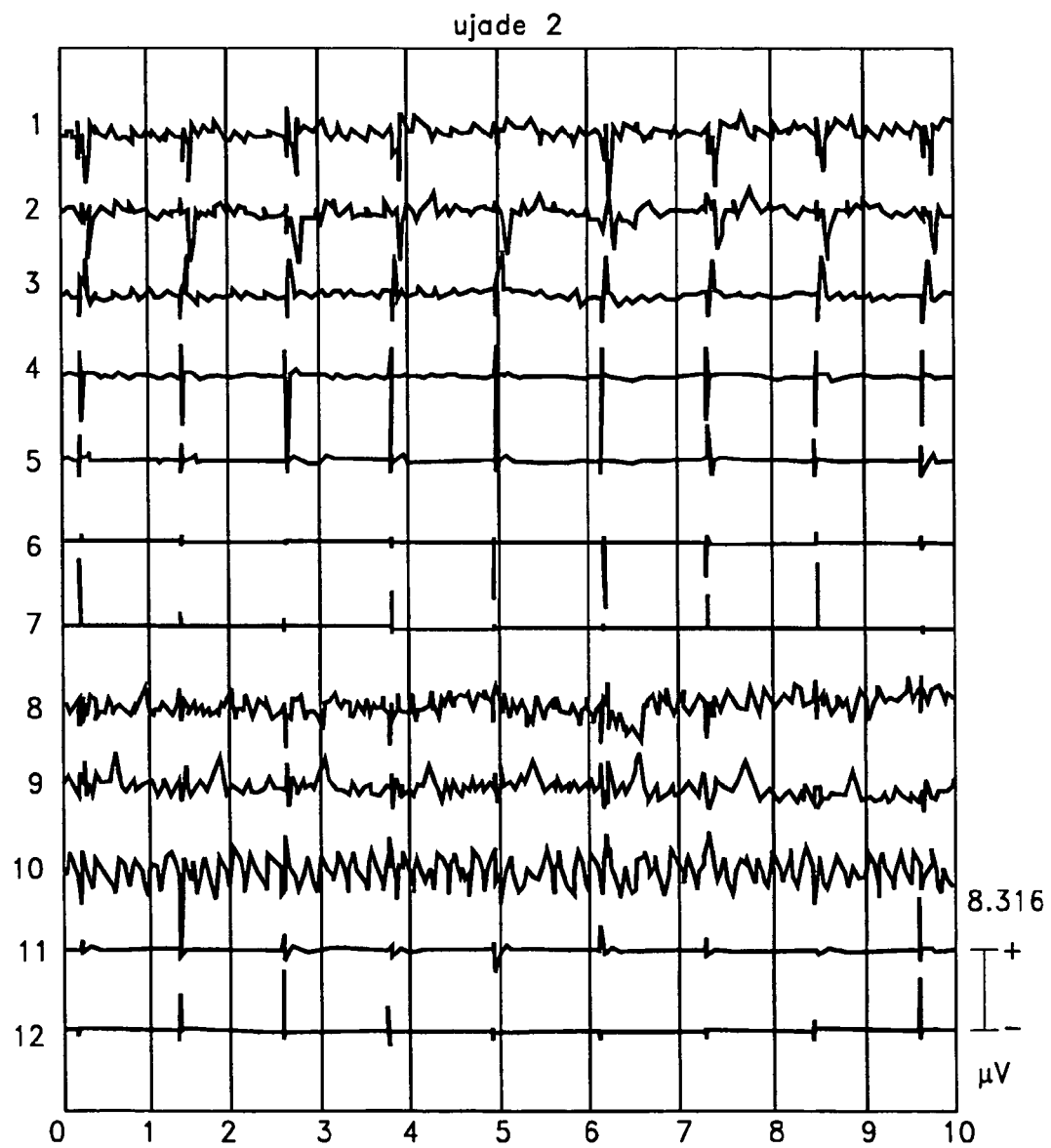
FIG. 3B is a sample chart of separated EKG signals.

In contrast, FIG. 3B illustrates output signals separated from the mixture signals of FIG. 3A, according to one embodiment of the present invention. As above, the horizontal axis in FIG. 3B represents time progression of ten seconds and the vertical axis represents the separated components 1 to 12. The separated signals in FIG. 3B are displayed as components 1 to 12 corresponding to the channels 1 to 12 in FIG. 3A, so that a physician can identify a separated signal as relating to its respective recorded signal's corresponding sensor location on the patient body. For example, in a standard 12-lead arrangement, leads II, III and AvF represent signals from the inferior region. Leads V1, V2 represent signals from the septal region. Leads V5, V6, I, and a VL represent signals from the lateral heart. Right and posterior heart regions typically require special lead placement for recording. To better identify the location of a heart condition, more than 12 leads can be used. For example, 20, 30, 40, 50, or even hundreds of sensors can be placed on various portions of a patient's torso. Fewer than 12 leads can also be used. The sensors are preferably non-invasive sensors located on the patient's body surface, but invasive sensors can also be used. With separated signals each corresponding to one of the locations, a physician can review the signals and detect abnormalities that correspond to the respective locations.

As shown in FIG. 3B, the component #1 represents the pacemaker signals and the early part of QRS complex signals. The component #2 represents major portions of later parts of the QRS complex signals. QRS complex signals represent the depolarization of the left ventricle. The component #10 represents atrial fibrillation (a type of arrhythmia) signals. Therefore atrial fibrillation is predicted to be located at the sensor location that corresponds to channel #10. Although components #1 and #10 contain similar frequency contents of oscillatory activity between heart beats, they capture activities from different spatial locations.

For EKG signals, we discovered that the signals separated using ICA are usually more independent from each other and have less information redundancy than signals that have not been processed through ICA. Compared to the recorded signals, the separated signals usually better represent the signals from the original sources of the patient's heart. In addition to arrhythmia, the separated cardiac signals can also be used to help detect other heart conditions. For example, the separated signals especially the separated QRS complex signals can be used detect premature ventricular contraction. The separated signals especially the separated Q wave signals can be used to detect myocardial infarction. Separating the EKG signals, especially separating the QRS complex and T wave signals, can help distinguish left and right bundle branch block.

Of course, the disclosed system and method are not limited to detecting arrhythmia, or any particular type of disease state. Embodiments of the invention include all methods of analyzing medical signals using ICA. For example, when a pregnant woman undergoes EKG recording, the heart signals from the woman and from the fetus(es) can be separated.

The separated cardiac signals can be characterized as non-random but not easily deterministic, which make them suitable subjects for chaotic analysis. As mentioned above, chaos theory (also called nonlinear dynamics) studies patterns that are not completely random but cannot be determined by simple formulas. The separated signals can be plotted to produce a chaos phase space portrait. By reviewing the patterns in the phase space portrait, including the existence and location of one or more attractors, a user is able to assess the likelihood of abnormality in the signals, which indicate disease conditions in the patient.

In a preferred embodiment, the QRS complex signals are separated into three different components, with each component representing a portion of the QRS complex. The 3 components are 3 data sets that are found to be temporally statistically independent using independent component analysis. Using the three components, a 3-dimensional phase space portrait of QRS complex can be displayed to show the trajectory of the three components.

Figure 3C:
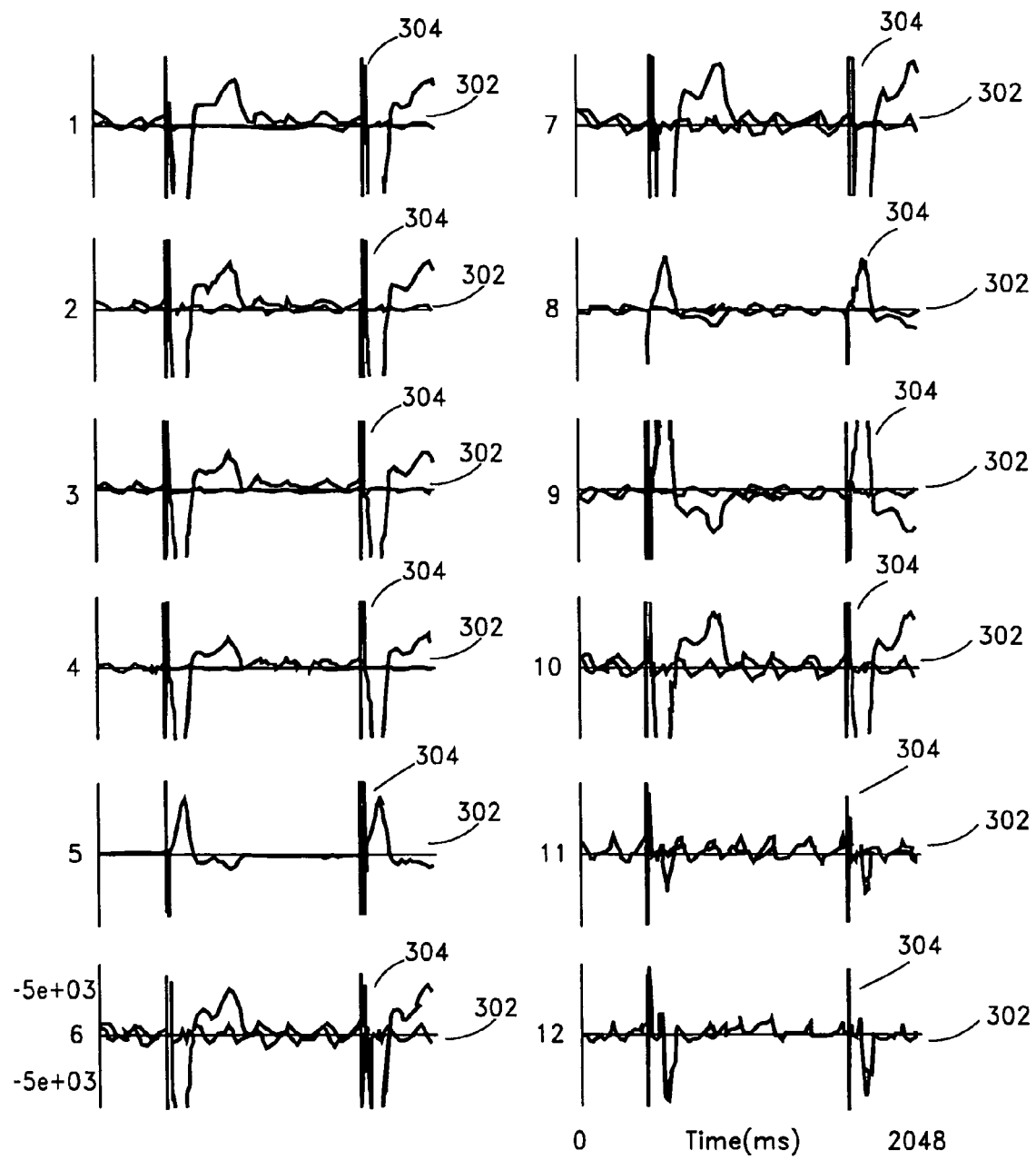
FIG. 3C is a sample chart of one component of separated signals back projected on the recorded signals.

FIG. 3C is a sample chart of the component #10 of separated signals (as shown in FIG. 3B) back projected onto the recorded signals of FIG. 3A. The separated signals of component #10, which indicate arrhythmia, is identified by reference number 302 in FIG. 3C. The 12 channels of recorded signals are identified by reference number 304 for ease of identification. FIG. 3C therefore allows direct visual comparison of a separated component against channels of recorded signals. The back projections of cardiac dynamics allow us to exam the amount of information accounted for by single or by multiple components in the recorded signals and to confirm the components' physiological meanings suggested by the surface topography (the aforementioned inverse of columns of the un-mixing matrix).

Figure 4A:
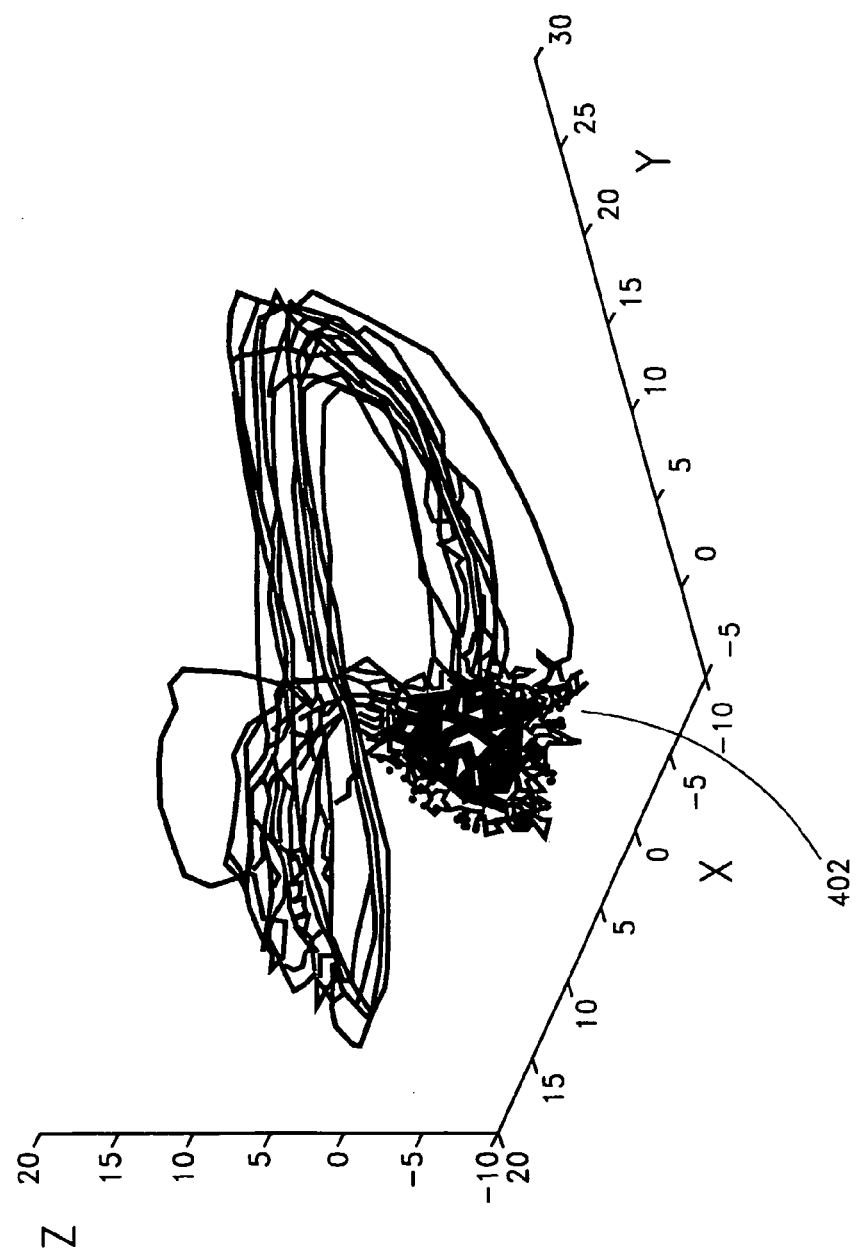
FIG. 4A is a chaos phase space portrait of three components of separated EKG signals of a healthy subject.
Figure 4B:
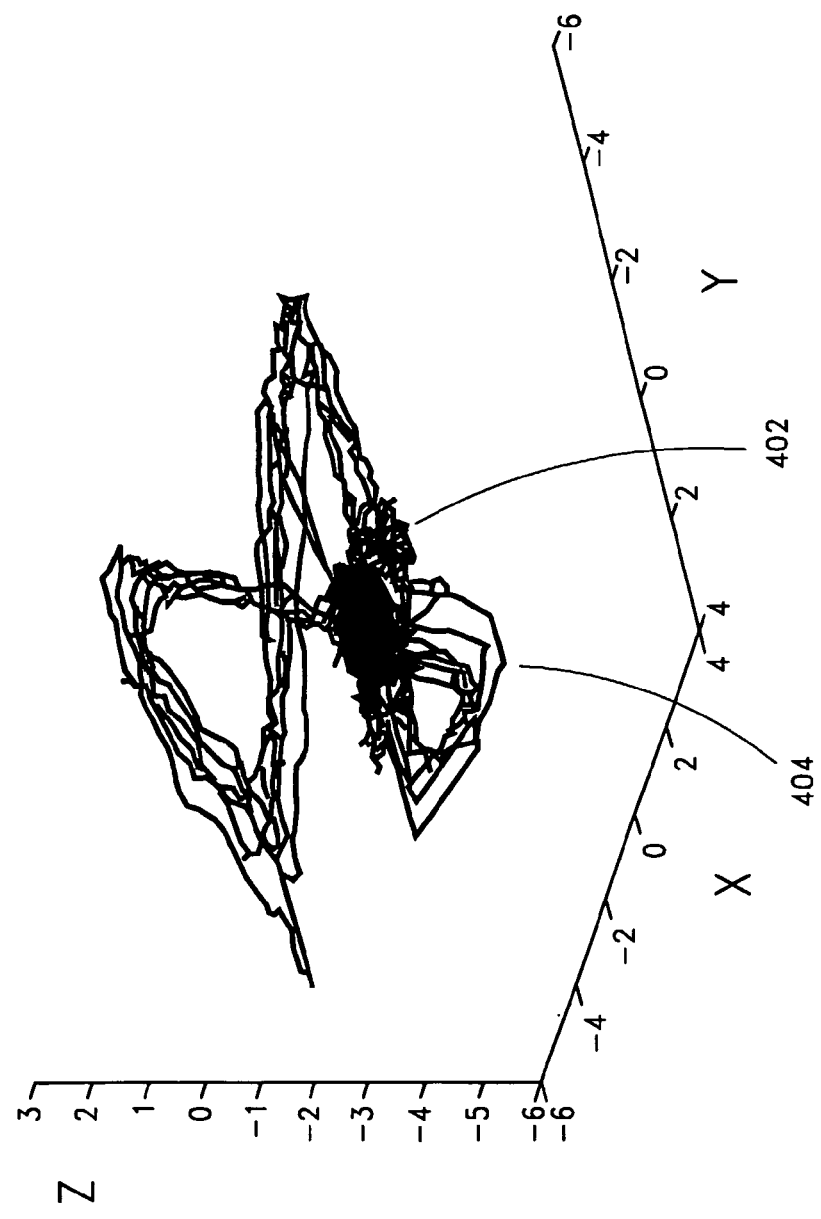
FIG. 4B is a chaos phase space portrait of three components of separated EKG signals of a subject with an abnormal heart condition.

FIG. 4A illustrates the phase space portrait of the EKG recording of a healthy subject. FIG. 4B illustrates the phase space portrait of the EKG recording of an atrial fibrillation patient. In FIGS. 4A and 4B, the x, y, and z axis represent the amplitudes of the 3 QRS components. The separated signals' values over time are plotted to produce the phase space portraits. In the healthy EKG recording of FIG. 4A, the dense cluster 402 indicates the existence of an attractor that attracts the signal values to the region of the dense cluster 402. The dense cluster 402 represents the most frequent occurrences of the signals. In the atrial fibrillation patient EKG recording of FIG. 4B, an additional loop 404, which is not part of the dense cluster 402, is below the attractor and the dense cluster 402 and closer to the base plane than the dense cluster 402. This additional loop 404 is presumably due to the oscillatory activity in the baseline portions of the EKG signals. The separated component #10 signal that indicate an arrhythmia condition is presumably responsible for the additional loop 404. The visual pattern can be compared with the visual pattern of a health subject and manually recognized as probative of indicating an abnormal condition such as atrial fibrillation.

Instead of the 3 QRS complex components as shown in FIG. 413, other components or more than 3 components can also be used to plot the chaos phase space portrait. If more than 3 components are used, the different components can be plotted in different colors. The 3 QRS complex components of FIG. 4B are selected because test results suggest that such a phase space portrait is physiological significant and functions usually well as an indication of a patient's heart condition.

Although FIGS. 3A, 3B, 4A and 4B were produced using test results related to the detection and localization of focal atrial fibrillation, the disclosed systems and methods can be used to detect and to localize other heart conditions including focal and re-entrant arrhythmia. The disclosed systems and methods can also be used to detect and to localize paroxysmal atrial fibrillation as well as persistent and chronic atrial fibrillation.

The disclosed methods can be used to improve existing cardioverter/defibrillators (ICD's) that can deliver electrical stimuli to the heart. In addition to existing ICD's and existing pacemakers, some of the existing cardiac rhythm management devices also combine the functions of pacemakers and ICD's. A computing module embodying the disclosed methods can be added to the existing systems to separate the recorded cardiac signals. The separated signals are then used by the cardiac rhythm management systems to detect or to predict abnormal conditions. Upon detection or prediction, the cardiac rhythm management system automatically treats the patient, for example by delivering pharmacologic agents, pacing the heart in a particular mode, delivering cardioversion/defibrillation shocks to the heart, or neural stimulation of the sympathetic or parasympathetic branches of the autonomic nervous system. Instead of or in addition to automatic treatment, the system can also issue a warning to a physician, a nurse or the patient. The warning can be issued in the form of an audio signal, a radio signal, and so forth. The disclosed signal separation methods can be used in cardiac rhythm management systems in hospitals, in patient's homes or nursing homes, or in ambulances. The cardiac rhythm management systems include implantable cardioverter defibrillators, pacemakers, biventricular or other multi-site coordination devices and other systems for diagnostic EKG processing and analysis. The cardiac rhythm management systems also include automatic external defibrillators and other external monitors, programmers and recorders.

In one embodiment, an improved cardiac rhythm management system includes a storage module that stores the separated signals. In one arrangement, the storage module can be removed from the cardiac rhythm management system and connected to a computing device. In another arrangement, the storage module is directly connected to a computing device without being removed from the cardiac rhythm management system. The computing device can provide further analysis of the separated signals, for example displaying a chaos phase space portrait using some of the separated signals. The computing device can also store the separated signals to provide a history of the patient's cardiac signals.

The disclosed methods can also be applied to predict the occurrence of arrhythmia within a patient's heart. After separating recorded EKG signals into separated signals, the separated signals can be matched with stored triggers and diagnosis as described above. If the separated signals match stored triggers that are associated with arrhythmia, an occurrence of arrhythmia is predicted. In other embodiments, an arrhythmia probability is then calculated, for example based on how closely the separated signals match the stored triggers, based on records of how frequently in the past has the patient's separated signals matched the stored triggers, and/or based on how frequently in the past the patient has actually suffered arrhythmia. The calculated probability can then be used to predict when will the next arrhythmia occur for the patient. Based on statistics and clinical data, calculated probabilities can be associated with specified time periods within an arrhythmia will occur.

In addition to EKG signals, the disclosed systems and methods can be applied to separate other electrical signals such as electroencephalogram signals, electromyographic signals, electrodermographic signals, and electroneurographic signals. They can be applied to separate other types of signals, such as sonic signals, optic signals, pressure signals, magnetic signals and chemical signals. The disclosed systems and methods can be applied to separate signals from internal sources, for example within a cardiac chamber, within a blood vessel, and so forth. The disclosed systems and methods can be applied to separate signals from external sources such as the skin surface or away from the body. They can also be applied to record and to separate signals from animal subjects.

Although the foregoing has described certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not to be limited by the preferred embodiments, but is to be defined by reference to the following claims.

The present application incorporates by reference U.S. Pat. No. 5,706,402, titled "Blind signal processing system employing information maximization to recover unknown signals through unsupervised minimization of output redundancy" filed Nov. 28, 1994 in its entirety as an APPENDIX as follows.

What is claimed is:

1. A medical system for processing electrocardiogram (EKG) signals, the medical system comprising:
    a receiving module configured to receive a plurality J of recorded EKG signals $X_j$ from a plurality of EKG sensors, one of the recorded EKG signals per one of the EKG sensors;
    a computing module configured to separate the received signals using independent component analysis to produce a plurality I of statistically independent separated signals $Y_i$;
    a display module configured to display the separated signals;
    a database storing a plurality of EKG signal triggers and one or more corresponding diagnoses, wherein at least one of the EKG signal triggers is based on history of the patient during an observation period; and
    a matching module configured to match the separated signals with one or more of the stored EKG signal triggers, the one or more of the stored EKG signal triggers comprising the at least one of the EKG signal triggers based on history of the patient during the observation period.

2. The medical system of claim 1, wherein the display module is further configured to display at least a portion of the separated signals in a chaos phase space portrait.

3. The medical system of claim 1, wherein the separated signals include three components of QRS complex, and wherein the display module is further configured to display at least the three QRS complex components in a chaos phase space portrait.

4. The medical system of claim 1, wherein the computing module is configured to separate the recorded signals by performing steps comprising multiplying a vector of the recorded signals by a matrix $W_{ij}$ such that $Y_i=W_{ij}*X_j$.

5. The medical system of claim 1, wherein the computing module is configured to separate the recorded signals using a neural-network implemented method, the neural-network implemented method comprising:
  selecting a plurality I of bias weights $W_{i0}$ and a plurality I*J of scaling weights $W_{ij}$;
  adjusting the bias weights $W_{i0}$ and the scaling weights $W_{ij}$ to minimize information redundancy among separated signals; and
  producing the statistically independent separated signals $Y_i$ such that $Y_i=W_{ij}*X_j+W_{i0}$.

6. The medical system of claim 1, wherein, when the matching module matches one of the EKG signal triggers to a particular diagnosis, the computing module causes the particular diagnosis to be displayed.

7. A computer-implemented method of processing electrocardiogram (EKG) recording signals, the method comprising:
  receiving a first plurality of EKG recording signals from EKG sensors placed on a patient, one of the EKG recording signals per one of the EKG sensors;
  separating the first plurality of EKG recording signals using independent component analysis to produce a second plurality of statistically independent separated signals;
  storing a plurality of EKG signal triggers and one or more diagnoses, each diagnosis of the one or more diagnoses corresponding to at least one EKG signal trigger of the plurality of EKG signal triggers, wherein the at least one of the EKG signal triggers is based on history of the patient during an observation period;
  matching the separated signals with one or more of the stored EKG signal triggers, the one or more of the stored EKG triggers comprising the at least one EKG signal trigger; and
  displaying the separated signals.

8. The method of claim 7, wherein the step of displaying the separated signals comprises displaying at least a portion of the separated signals in a chaos phase space portrait.

9. The method of claim 7, wherein the patient is a pregnant patient, and wherein the separated signals include separated signals originating from the pregnant patient and separated signals originating from a fetus.

10. The method of claim 7, further comprising calculating probability of arrhythmia in the patient based on separation of the separated signals from a match of one or more stored arrhythmia triggers.

11. The method of claim 7, wherein the displayed separated signals are used by a physician to determine the likelihood of myocardial infarction in the patient.

12. The method of claim 7, wherein each of the separated signals corresponds to a location on the patient body, wherein the displayed separated signals are used by a physician to determine the location of an abnormal heart condition in the patient according to the separated signals' corresponding locations.

13. A cardiac rhythm management system comprising:
  a cardiac signal recording module configured to record cardiac signals of a patient;
  a computing module configured to separate the recorded cardiac signals into statistically independent separated signals using independent component analysis;
  a detection module configured to detect or predict an abnormal condition based on analyzing the separated cardiac signals; and
  a treatment module configured to treat the patient when the abnormal condition is detected or predicted;
  wherein the detection module is configured to detect the abnormal condition by comparing the separated signals with a stored trigger to determine whether the separated signals match the stored trigger;
  the treatment module is configured to deliver one or more electrical stimuli to heart of the patient in response to detection or prediction of the abnormal condition by the detection module; and
  the stored trigger is based on history of the patient.

14. A cardiac rhythm management system comprising:
  a cardiac signal recording module configured to record cardiac signals of a patient;
  a computing module configured to separate the recorded cardiac signals into statistically independent separated signals using independent component analysis;
  a detection module configured to detect or predict an abnormal condition based on analyzing the separated cardiac signals; and
  a warning module configured to issue a warning when the abnormal condition is detected or predicted;
  wherein:
    the detection module is configured to detect or predict the abnormal condition by comparing the separated signals with at least one stored trigger to determine whether the separated signals match the at least one stored trigger;
    the treatment module is configured to deliver one or more electrical stimuli to heart of the patient in response to detection or prediction of the abnormal condition by the detection module; and
    the stored trigger is based on history of the patient.

15. The cardiac rhythm management system of claim 14, wherein the at least one stored trigger comprises a plurality of stored triggers.

* * * * *